US008871266B2

(12) United States Patent
Crittenden et al.

(10) Patent No.: US 8,871,266 B2
(45) Date of Patent: Oct. 28, 2014

(54) PROBIOTIC STORAGE AND DELIVERY

(75) Inventors: Ross Crittenden, Werribee (AU); Luz Sanguansri, Werribee (AU); Mary Ann Augustin, Werribee (AU)

(73) Assignee: Commonwealth Scientific & Industrial Research Organisation, Campbell, Australian Capital Territory (AU)

( * ) Notice: Subject to any disclaimer, the term of this patent is extended or adjusted under 35 U.S.C. 154(b) by 1845 days.

(21) Appl. No.: 10/573,784

(22) PCT Filed: Mar. 30, 2004

(86) PCT No.: PCT/AU2004/001341
§ 371 (c)(1), (2), (4) Date: Mar. 28, 2006

(87) PCT Pub. No.: WO2005/030229
PCT Pub. Date: Apr. 7, 2005

(65) Prior Publication Data
US 2007/0122397 A1 May 31, 2007

(30) Foreign Application Priority Data

Oct. 1, 2003 (AU) .................................. 2003905338

(51) Int. Cl.
| | | |
|---|---|---|
| *C12N 1/00* | (2006.01) | |
| *C12N 1/04* | (2006.01) | |
| *C12N 1/12* | (2006.01) | |
| *C12N 11/00* | (2006.01) | |
| *C12N 11/16* | (2006.01) | |
| *C12P 1/00* | (2006.01) | |
| *C12P 1/04* | (2006.01) | |
| *C12P 7/00* | (2006.01) | |
| *C12P 19/00* | (2006.01) | |
| *C12P 39/00* | (2006.01) | |
| *A61K 36/064* | (2006.01) | |
| *A61K 35/74* | (2006.01) | |
| *A61K 47/42* | (2006.01) | |
| *A61K 47/26* | (2006.01) | |
| *A61K 47/44* | (2006.01) | |
| *A61K 9/19* | (2006.01) | |

(52) U.S. Cl.
CPC .............. *A61K 47/26* (2013.01); *A61K 36/064* (2013.01); *A61K 35/745* (2013.01); *A61K 47/42* (2013.01); *A61K 35/741* (2013.01); *A61K 35/747* (2013.01); *A61K 35/744* (2013.01); *A61K 47/44* (2013.01); *A61K 9/19* (2013.01); *Y10S 435/822* (2013.01); *Y10S 435/853* (2013.01); *Y10S 435/885* (2013.01); *Y10S 435/886* (2013.01)
USPC ...... 424/484; 424/93.1; 424/93.4; 424/93.44; 424/93.45; 435/41; 435/42; 435/72; 435/132; 435/170; 435/174; 435/243; 435/252.1; 435/260; 435/822; 435/853; 435/885; 435/886

(58) Field of Classification Search
CPC .................... A23V 2002/00; A23V 2200/224; A23V 2250/54246; A23V 2250/1868; A23V 2250/187; A23V 2250/1872; A23V 2250/5034; A23V 2250/5062; A23V 2250/61; A23V 2200/254; A23V 2250/044; A23V 2250/2136; A23V 2250/242; A23V 2250/2482
See application file for complete search history.

(56) References Cited

U.S. PATENT DOCUMENTS

| | | | | |
|---|---|---|---|---|
| 6,500,463 | B1 * | 12/2002 | van Lengerich | ............... 424/499 |
| 7,115,297 | B2 * | 10/2006 | Stillman | ....................... 426/590 |
| 2003/0152629 | A1 | 8/2003 | Shafer et al. | |

FOREIGN PATENT DOCUMENTS

| | | |
|---|---|---|
| EP | 0904784 A1 | 3/1999 |
| EP | 1 281 752 | 2/2003 |
| JP | 02-142735 | 5/1990 |
| JP | 04-082827 | 3/1992 |
| JP | 07-069867 | 3/1995 |
| JP | 2000-063289 | 2/2000 |
| WO | WO-96/08261 | 3/1996 |
| WO | WO 99/17788 A1 | 4/1999 |
| WO | WO-99/48372 | 9/1999 |
| WO | WO-01/25414 | 4/2001 |
| WO | WO-01/74175 | 10/2001 |
| WO | WO 01/85774 A1 | 11/2001 |
| WO | WO 02/15720 * | 2/2002 |
| WO | WO 03/010297 A1 | 2/2003 |
| WO | WO 03/010299 A1 | 2/2003 |
| WO | WO 03/026687 A1 | 4/2003 |
| WO | WO-03/075676 | 9/2003 |
| WO | WO-2005/030229 | 4/2005 |

OTHER PUBLICATIONS

Kailasapathy, Kaila, "Microencaptulation of Probiotic Bacteria: Technology and Potential Applications," Current Issues in Intestinal Microbiology, 3(2), 2002, 39-48.
Krasaekoopt, Winwusa et al., "Evaluation of encapsulation techniques of probiotics for yoghurt," International Dairy Journal, 13, 2003, 3-13.
Communication from European Patent Office received in EP 04 761 376.5-2403, 2011.

* cited by examiner

*Primary Examiner* — Debbie K Ware
(74) *Attorney, Agent, or Firm* — Foley & Lardner LLP (57) ABSTRACT

Probiotic microorganisms are micro encapsulated by dispersing the probiotic microorganism in an aqueous suspension of a film forming protein and a carbohydrate; in an oil in water emulsion of a film forming protein and a carbohydrate and a fat; or in an oil which is subsequently dispersed in a film forming protein and a carbohydrate. The emulsion or suspension may be dried to form a powder. The probiotic may be dispersed in oil and then emulsified with the aqueous suspension and then dried to produce an encapsulated oil be dried to produce a powder. Oil suspended probiotics may be preferred where the probiotic is water sensitive. The preferred protein is casein or whey protein and the carbohydrate may be a resistant starch or a saccharide with a reducing sugar group. Where the probiotic is oxygen sensitive the protein carbohydrate is heated to create Maillard reaction products in the encapsulating film.

15 Claims, 8 Drawing Sheets

LEGEND

○ — Non-encapsulated (freeze dried probiotic sample)

□ — Encapsulated: protein sugar

▲ — Encapsulated: protein - RS(Raw)

● — Encapsulated: protein -sugar MRP

△ — Encapsulated: protein - RS (MF)

◆ — Encapsulated: (in oil) protein - sugar MRP

◊ — Encapsulated:(in protein) sugar MRP-oil emulsion

■ — Encapsulated: (in protein)-RS (MF)-oil emulsion

PROBIOTIC STORAGE AND DELIVERY

This invention relates to the storage and delivery of probiotic materials to selected sites in the gastrointestinal system.

BACKGROUND TO THE INVENTION

Probiotics are live microbial food ingredients that have a scientifically documented beneficial effect on human health. Probiotics are also used in animal feedstuffs either to improve animal health or productivity. They are used in pet foods, mainly to decrease unpleasant odours and improve consistency of fecal material.

Most of the dominant global strains of commercial probiotic bacteria belong to the bifidobacteria and the lactobacilli. However, bacteria from other genera are used in some parts of the world. For example, China uses a number of other genera, including *Bacillus* and a *Clostridium*. *Enterococcus faecium* has also been used worldwide, however, this genus is implicated in transfer of antibiotic resistance. In the Western world, both bifidobacteria and lactobacilli have a strong track record as safe and acceptable genera to use as probiotics. Other examples are discussed in:

Mogensen, G., Salminen, S., O'Brien, J., Ouwehand, A., Holzapfel, W., Shortt, C., Fonden, R., Miller, G D., Donohue, D., Playne, M., Crittenden, R., Bianchi-Salvadori, B. and R. Zink (2002). Food microorganisms—health benefits, safety evaluation and strains with documented history of use in foods *Internat, Dairy Federation Bulletin No:* 377: 4-9 and Mogensen, G., Salminen, S., O'Brien, J., Ouwehand, A., Holzapfel, W., Shortt, C., Fonden, R., Miller, G D., Donohue, D., Playne, M., Crittenden, R., Bianchi-Salvadori, B. and R. Zink (2002) Inventory of microorganisms with a documented history of use in food *Internat, Dairy Federation Bulletin No:* 377: 10-19.

It has been widely recognized by researchers and medical investigators that most health effects are conferred by a specific strain, and mostly not by the species in general. While many research groups have selected strains for useful probiotic properties for manufacture, for incorporation into foods, for survival in the gut, and for health properties, there is a dearth of information on performance in humans published in peer-reviewed journals.

Evidence is increasing that a probiotic food should contain selected strains of both lactobacilli and bifidobacteria. The concept is that the probiotic lactobacilli are useful in the young (where the gut microflora of infants is already naturally rich in bifidobacteria), and that addition of probiotic bifidobacteria becomes more important in the elderly. The numbers of indigenous bifidobacteria decline with aging if probiotics are not used. Bifidobacteria provide some protection against pathogens which are not able to be done effectively by lactobacilli alone. Adequate viable numbers of the strain of probiotic bacteria in the appropriate segment of the gut are essential if they are to be effective in an health sense. Most authorities consider 10 million bacteria per gram of food an appropriate dietary dose. Technically, this can be quite readily achieved. However, dose response curves have not been produced for any probiotic strain against any health condition.

Losses of bacterial numbers occur during manufacture, freeze drying and during shelf life. However, further losses occur during transit through the gastro-intestinal tract. The probiotic cultures will encounter gastric juices in the stomach ranging from pH 1.2 (on an empty stomach) through to pH 5.0. The cultures will be present in the stomach from around 40 minutes up to 5 hours. They will also encounter in the stomach and the small intestine, bile salts, lipolytic, hydrolytic and proteolytic enzymes, which are also able to kill bacteria. It is not until the probiotic bacteria reach higher pH regions of the gastro-intestine that they are able to grow or survive. Such regions are the ileum and the bowel. During this transit, the bacteria also have to compete with resident bacteria for space and for nutrients. They also have to avoid being flushed out of the tract by normal peristaltic action, and they have to avoid being killed by anti-microbials produced by other organisms. The bacteria have their most favourable growing conditions in the first third of the large bowel (the proximal bowel).

Ability to adhere to surfaces, such as intestinal mucosal layer, and the epithelial cell walls of the gut are thus important characteristics for a probiotic. The term "colonisation" is used, and means that the bacteria has mechanisms which enable it to survive in a region of the gastro-intestine on an on-going basis. It is generally believed that the microflora of the gastro-intestine are relatively stable in adults, and are not easily altered by changes in the conditions in the gut ecosystem.

Exceptions to this are administration of antibiotics, but even then the gut flora usually re-establish after sometime with a similar species composition.

Mechanisms of Action of probiotic bacteria include:
competitive exclusion (occupation of niches in the gut mucosal surface to prevent colonisation by infective species)
production of acid conditions (lactic acid fermentation by the bacteria leading to lowered gut pH)
effects on immune-mediated response
reduction of putrefactive and genotoxic intestinal reactions (leading to lower pre-carcinogen levels)
release of anti-microbials, such as bacteriocins Many diarrhoeal diseases originate from dysfunction in the small intestine, yet probiotic bacteria are not usually found in high numbers in that region, with the exception of some lactobacilli. There is little direct evidence available from healthy humans on microbial composition of the small intestine region. However, the effectiveness of probiotic bacteria in reducing diarrhoeal disease is quite well established. They are either functioning in transit through the small intestine, or acting through an immune effect. Most immune reactions will occur in the mucosal walls of the small intestine and not the large bowel, thus, if immune-modulation is believed to be the mechanism of action, then the probiotic must be present in the small intestine. The other region of diarrhoeal disturbance is the large bowel. Probiotic bacteria can establish in that region quite easily.

In addition to diarrhoeal disorders, probiotic bacteria are effective in lessening lactose intolerance, provided bacteria are chosen which have high beta galactosidase enzyme function. Lactose intolerance effects manifest in the bowel. There are a large number of other emerging health claims made for probiotics. These centre particularly around the bowel eg., bowel cancer, irritable bowel syndrome and inflammatory bowel diseases (such as Crohn's disease). Accordingly, release of probiotic lactobacilli in the last half of the small intestine is preferred. Release of bifidobacteria is usually aimed to occur in the large bowel. Greater immune responses tend to occur with bifidobacteria than with lactobacilli, thus, there is an argument that bifidobacteria in the small intestinal regions are of great importance.

Daily consumption of the probiotic is necessary if the target site is in the small intestine, as it is unlikely that the bacteria can adhere to the gut wall in sufficient numbers (except perhaps some lactobacilli). However, daily consumption may not be necessary if the target site is the large bowel, as growth of the bacteria and colonisation may occur.

Probiotic bacteria with good characteristics for effectiveness against disease and other conditions may not have good survival characteristics (eg resistance to low pH, bile salts, proteolytic and hydrolytic enzymes, resistance to antibiotics, adherence to cell walls). Protection of the bacteria during transit to the target site is usually necessary.

Protection may be achieved in several ways: encapsulation in a slow release pharmaceutical compound; encapsulation in a gum or in alginate; encapsulation in a resistant starch or in inulin in combination with a gum; protection by incorporation in a food containing resistant starch; or in a dairy food where the proteins and fats may provide some protection.

U.S. Pat. No. 5,422,121 discloses a coating incorporating a film forming polymer having hydrophilic groups and a polysaccharide decomposable in the colon which is useful in delivering dosages to the colon.

U.S. Pat. No. 5,840,860 discloses the delivery of short chain fatty acids to the colon by covalently linking them to a carbohydrate carrier.

U.S. Pat. No. 6,060,050 discloses a combination of a probiotic bacteria such as *bifidobacterium* with high amylose starch as a carrier which also acts as a growth or maintenance medium in the large bowel or other regions of the gastrointestinal tract.

U.S. patent application 20030096002 discloses a matrix for use in the controlled release of microorganisms. The matrix is formed of a hydrophobic wax and a release modifying agent selected from polysaccharides, starch, an algae derivative or a polymer.

U.S. Pat. No. 6,413,494 discloses a colonic drug delivery vehicle consisting of a polysaccharide such as pectin.

Some probiotics need protection during processing as well as during delivery to the gastro intestinal tract. They may be water or oxygen sensitive and need protection to maintain viability during processing storage and transporting. European patent 1213347 discloses a method of drying and preserving yeasts and microorganisms by mixing them with a matrix material that absorbs water It is an object of this invention to provide a means of encapsulating probiotics to protect them from deterioration during processing and storage and enable them to be delivered to specific sites in the gastrointestinal tract.

BRIEF DESCRIPTION OF THE INVENTION

To this end the present invention provides probiotic bacteria formulations in which one or more probiotic microorganisms are dispersed
  a) in an aqueous suspension of a protein and a carbohydrate.
  b) in an oil in water emulsion of a film forming protein and a carbohydrate and a fat, or
  c) in an oil which is subsequently dispersed in a film forming protein and a carbohydrate The suspension, dispersion or emulsion may be dried to form a powder. Throughout this specification the term probiotic is intended to include microorganisms such as bacteria or fungi either individually or in combination which exhibit a beneficial effect on human health if delivered, preferably alive to the target region of the gut. Examples include bifido bacteria, lactobacilli, *saccharomyces*, lactococci, streptococci, propionibacteria and any other microorganisms which may be demonstrated to have beneficial effects on the host. The probiotic may be mixed with a prebiotic material or be part of a symbiotic or synbiotic material.

Throughout this specification the term prebiotic means a substance such as a protein, peptide, or carbohydrates that provide nutrients for the probiotic or assist the probiotic. For example lactoferrin can enhance the growth of desirable bacteria. Usually prebiotics cannot be digested in the upper intestinal tract. Prebiotic carbohydrates include resistant starch, potato starch or high amylose starch such as Starplus, modified starches (including carboxylated starches, acetylated, propionated, and butyrated starches), non-digestible oligosaccharides such as fructo-, gluco-, xylo-, soyabean-, galacto-, milk-, inulin-, arabinoxylans, arabinogalactans, galatomannans or digestion products of these, but not excluding other oligosaccharides able to exert prebiotic effects.

Throughout this specification the term symbiotic or synbiotic means a combination of a probiotic and a prebiotic which together have a synergistic beneficial effect on human health.

The probiotic bacteria may be introduced to the encapsulating medium as a liquid concentrate or in freeze dried form. The probiotic bacteria may be dispersed in oil and then emulsified with the aqueous suspension and then dried to produce an encapsulated oil carrying probiotic. This may also be dried to produce a powder. Any suitable drying technology such as spray drying, freeze drying or refractive windows drying may be used. Oil suspended probiotics may be preferred where the probiotic is moisture sensitive. The oil is preferably an edible oil and the emulsion or the powder obtained by drying the emulsion, may be used as a food ingredient, as well as in feed supplements.

The aqueous suspension of the carbohydrate and the film forming protein or an emulsion of a film forming protein carbohydrate and oil mixture may be heated before the encapsulation step to react the saccharide and protein components. If the saccharide has reducing sugar groups the heating step will produce maillard reaction products. Heated aqueous suspensions are preferred when the probiotic is oxygen sensitive.

The encapsulants of this invention form stable robust films or matrices which embed the probiotic or form films around the probiotic or the oil droplets. Any protein useful in encapsulating oils can be used as the protein component of this invention. A carbohydrate is combined with the protein. In an aqueous suspension the protein need not be a film forming protein as it forms an encapsulating matrix about the probiotic. However with oil based systems a film forming protein is required.

The protein is preferably soluble and is preferably stable in the heating range of the Maillard reaction and includes casein, soy and whey proteins, gelatine, egg albumin and hydrolysed proteins with increased free amino acid groups including soy protein hydrolysate. Care needs to be taken in reacting the protein and carbohydrate to ensure that the conditions do not result in gelling or coagulation of the protein, as this will render the protein incapable of forming an effective film. The preferred protein is a milk protein especially casein or whey protein isolate. Casein is a preferred protein in many applications because of its low cost and its greater resistance to gelling during any heat treatment eg: to form Maillard reaction products. For infant food applications whey proteins are the preferred protein source. The amount of Maillard reaction product in the protein-carbohydrate mixture is an amount sufficient to provide oxygen scavenging activity for the period of the product's shelf life. The minimum reaction required between the protein and carbohydrate prior to encapsulation will depend on the oxygen tolerance of the specific probiotic strain that is encapsulated. The extent of Maillard reaction product formed can be monitored, for a particular protein/carbohydrate combination, by the degree of colour change that occurs. An alternative measure is to assay the unreacted sugar.

It is not essential that the carbohydrate and protein undergo a Maillard reaction to be an effective encapsulant for the probiotic bacteria. In mixing the protein and starch it has been found that microfluidisation of the materials particularly the carbohydrate enhances the effectiveness of the formulation.

A preferred carbohydrate is a sugar with a reducing group preferably selected from the group consisting of monosaccharides (eg: glucose, fructose), disaccharides (eg: maltose, lactose), trisaccharides, oligosaccharides and glucose syrups. Any reducing sugar source may be used including honey. Carbohydrates that do not undergo a Maillard reaction with the protein may also be used.

It is within the ambit of this invention to use an oligosaccharide, or a starch including a resistant starch to improve the delivery and growth of the probiotic in the intestine and colon. Some of these materials are usually not digested in the upper intestinal tract and can assist in the growth of the probiotic.

DETAILED DESCRIPTION OF THE INVENTION

Preferred embodiments of the invention will be described. In the drawings

MATERIALS

Probiotic bacteria used in the examples are bifidobacteria and lactobacilli, however other strains of probiotic bacteria and blends can also be encapsulated by the same process.

A probiotic *Lactobacillus acidophilus* La-5 (Chr. Hansen, Denmark) and two strains of probiotic bifidobacteria with inherently different resiliencies to environmental conditions were used to investigate the advantages of the microencapsulation techniques. *Bifidobacterium lactis* Bb-12 (Chr. Hansen, Denmark) is a relatively robust probiotic strain with a relatively high resilience to environmental conditions including low pH, and a relatively high aerotolerance. *Bifidobacterium infantis* (Chr. Hansen, Denmark) is relatively sensitive to environmental conditions in comparison to *Bifidobacterium lactis* Bb-12.

Protein used in the examples is mainly casein, however the protein in the formulations can easily be substituted for other proteins such as whey protein, soy protein, hydrolysed proteins, etc.

Carbohydrates used in the examples include glucose, oligosaccharides, dried glucose syrup, resistant starches and pre-processed starches. Other carbohydrates can be used in the formulations such as lactose, polysaccharides, maltodextrins, native starches, modified starches etc.

Lipids (vegetable and animal oils, di- and tri-glycerides, n3- and n6 oils, etc.)

Microencapsulation Strategies Used

Strategy 1: Probiotic Bacteria in an Aqueous Suspension of a Reacted or Unreacted Protein and a Carbohydrate.

Prepare a mixture of a protein-carbohydrate solution at 60° C. (where the carbohydrate includes a resistant starch, the starch may be used as is or pre-processed by microfluidisation). Heat the mixture at 98° C. for 30 min. Cool down to 10° C. Disperse the freeze dried bacteria or concentrate into the reacted solution using a mixer. Spray dry at 120-160° C. $T_i$, and/50-70° C. $T_o$ Temperature of the inlet air $T_i$ inlet air temperature, Temperature of the outlet air $T_o$).

Prepare a mixture of a protein-carbohydrate solution at 60° C. (where the carbohydrate includes a resistant starch, the starch may be used as is or pre-processed by microfluidisation). Cool down to 10° C. Disperse freeze dried bacteria or concentrate into the solution using a mixer. Spray dry at 120-160° C. $T_i$ and/50-70° C. $T_o$.

Strategy 2: Probiotic Bacteria in Reacted or Unreacted Oil-in-Water Emulsion of a Film Forming Protein and a Carbohydrate and a Fat.

Prepare a mixture of a protein-carbohydrate solution at 60° C. (where the carbohydrate includes a resistant starch, the starch may be used as is, or pre-processed by microfluidisation), add the oil and homogenise the mixture at 350 bar. Heat the homogenised emulsion at 98° C. for 30 min. Cool down to 10° C. Disperse freeze dried bacteria into the reacted mixture using a mixer. Spray dry at 120-160° C. $T_i$, and/50-70° C. $T_o$.

Prepare a mixture of a protein-carbohydrate solution at 60° C. (where the carbohydrate includes a resistant starch, the starch may be used as is, or pre-processed by microfluidisation), add the oil and homogenise the mixture at 250 bar. Cool down to 10° C. Disperse the freeze dried bacteria in to the mixture using a mixer. Spray dry at 120-160° C. $T_i$ and/50-70° C. $T_o$.

Strategy 3: Probiotic Bacteria in an Oil That is Subsequently Dispersed in Reacted or Unreacted Film Forming Protein and a Carbohydrate.

Prepare a mixture of a protein-carbohydrate solution at 60° C. (where the carbohydrate includes a resistant starch, the starch may be used as is, or pre-processed by microfluidisation). Heat the mixture at 98° C. for 30 min. Cool down to 10° C. Disperse freeze dried bacteria in oil. Add the freeze dried bacteria dispersion into the reacted solution using a mixer. Spray dry at 120-160° C. $T_i$, and/50-70° C. $T_o$.

Prepare a mixture of a protein-carbohydrate solution at 60° C. (where the carbohydrate includes a resistant starch, the starch may be used as is, or pre-processed by microfluidisation). Cool down to 10° C. Disperse freeze dried bacteria in oil. Add the freeze dried bacteria dispersion into the solution using a mixer. Spray dry at 120-160° C. $T_i$, and/50-70° C. $T_o$.

PROCESSING AND FORMULATION EXAMPLES

Strategy 1

Example 1

Encapsulated: Protein-Sugar

Freeze dried probiotic bacteria encapsulated in protein-sugar matrix

Processing Steps

Prepare a mixture containing sodium caseinate, oligosaccharide and dried glucose syrup (Cas-oligo-DGS) solution at 60° C. Cool down to 10° C. Disperse freeze dried bacteria into the solution using a mixer. Spray dry at 160/65° C. $T_i/T_o$.

| Ingredient | % in powder | % in emulsion |
|---|---|---|
| Formulation 1 | | |
| Freeze dried bacteria | 20% | 5.9% |
| Cas-Oligo-DGS Blend | 80% | 23.5% |
| Water | | 70.6% |
| Total | 100% | 100.0% |
| Formulation 2 | | |
| Freeze dried bacteria | 11.8% | 2.9% |
| Cas-Oligo-DGS Blend | 88.2% | 22.1% |
| Water | | 75% |
| Total | 100% | 100.0% |

Example 2

Encapsulated: Protein-Sugar MRP

Freeze dried probiotic bacteria encapsulated in heat reacted protein-sugar matrix Processing Steps Prepare a mixture containing sodium caseinate, oligosaccharide and dried glucose syrup (Cas-oligo-DGS) solution at 60° C. Heat mixture at 98° C. for 30 min Cool down to 10° C. Disperse freeze dried bacteria into the reacted solution using a mixer. Spray dry at 160/65° C. $T_i/T_o$.

| Ingredient | % in powder | % in emulsion |
|---|---|---|
| Formulation 1 | | |
| Freeze dried bacteria | 20% | 5.9% |
| Heat processed Cas-Oligo-DGS Blend | 80% | 23.5% |
| Water | | 70.6% |
| Total | 100% | 100.0% |
| Formulation 2 | | |
| Freeze dried bacteria | 11.8% | 2.9% |
| Heat processed Cas-Oligo-OGS Blend | 88.2% | 22.1% |
| Water | | 75% |
| Total | 100% | 100.0% |

Example 3

Encapsulated: Protein-Sugar-RS(Raw)

Freeze dried probiotic bacteria encapsulated in protein-sugar-high amylose starch matrix Processing Steps Prepare a 15% w/w sodium caseinate solution at 60° C., then add the sugar.

Prepare a 10% w/w Hylon VII dispersion at 60° C. Mix the sodium caseinate-sugar solution and Hylon VII dispersion together. Cool down to 10° C. Add the freeze dried bacteria into the protein-sugar-starch mixture using a mixer. Spray dry at 160/65° C. $T_i/T_o$.

| Ingredient | % in powder | % in emulsion |
|---|---|---|
| Freeze dried bacteria | 11.8% | 2.2% |
| Na Caseinate | 29.4% | 5.4% |
| Oligosaccharide | 29.4% | 5.4% |
| Water | | 81.5% |
| Hylon VII | 29.4% | 5.4% |
| Total | 100.0% | 100.0% |

Example 4

Encapsulated: Protein-Sugar-RS(MF)

Freeze dried probiotic bacteria encapsulated in protein-sugar-microfluidised high amylose starch matrix Processing Steps Prepare a 15% w/w protein solution at 60° C., then add the sugar. Prepare 20% w/w Hylon VII dispersion at 60° C., heat 121° C. for 60 min, cool down, and add remaining water to make up to 10% w/w total solids and microfluidise at 800 bar×3 passes. Mix the protein-sugar solution and microfluidised Hylon VII dispersion together. Cool down to 10° C. Add the freeze dried bacteria into the protein-sugar-starch mixture using a mixer. Spray dry at 160/65° C. $T_i/T_o$.

| Ingredient | % in powder | % in emulsion |
|---|---|---|
| Freeze dried bacteria | 11.8% | 2.2% |
| Na Caseinate | 29.4% | 5.4% |
| Oligosaccharide | 29.4% | 5.4% |
| Water | | 81.5% |
| Hylon VII | 29.4% | 5.4% |
| Total | 100.0% | 100.0% |

Example 5

Encapsulated: Protein-Sugar-Oil Emulsion

Freeze dried probiotic bacteria encapsulated in protein-sugar-oil emulsion

Processing Steps

Prepare a mixture containing sodium caseinate, oligosaccharide and dried glucose syrup (Cas-oligo-DGS) solution at 60° C., add oil using a mixer and homogenise at 250 bar. Cool down to 10° C. Disperse freeze dried bacteria into the emulsion using a mixer. Spray dry at 160/65° C. $T_i/T_o$.

| Ingredient | % in powder | % in emulsion |
|---|---|---|
| Freeze dried bacteria | 20% | 5.9% |
| Cas-Oligo-DGS Blend | 72% | 21.2% |
| Water | | 70.6% |
| Oil | 8% | 2.3% |
| Total | 100% | 100.0% |

Example 6

Encapsulated: Protein-Sugar-Oil MRP Emulsion

Freeze dried probiotic bacteria encapsulated in heat reacted protein-sugar-oil emulsion Processing Steps Prepare a mixture containing sodium caseinate, oligosaccharide and dried glucose syrup (Cas-oligo-DGS) solution at 60° C., add the oil and homogenise at 250 bar. Heat the emulsion at 98° C. for 30 min. Cool down to 10° C. Disperse freeze dried bacteria into the emulsion using a mixer. Spray dry at 160/65° C. $T_i/T_o$.

| Ingredient | % in powder | % in emulsion |
|---|---|---|
| Formulation 1 | | |
| Freeze dried bacteria | 20% | 5.9% |
| Cas-Oligo-DGS Blend | 72% | 21.2% |
| Water | | 70.6% |
| Oil | 8% | 2.3% |
| Total | 100% | 100.0% |
| Formulation 2 | | |
| Freeze dried bacteria | 8% | 2% |
| Cas-Oligo-DGS Blend | 60% | 15% |
| Water | | 75% |
| Oil | 32% | 8% |
| Total | 100% | 100.0% |

Example 7

Encapsulated: Protein-Sugar-RS(MF)-Oil Emulsion

Freeze dried probiotic bacteria encapsulated in protein-sugar-microfluidised high amylose starch-oil emulsion
Processing Steps Prepare a 15% w/w protein solution at 60° C., then add the sugar. Prepare 20% w/w Hylon VII dispersion at 60° C., heat 121° C. for 60 min, cool down, and add remaining water to make up to 10% w/w total solids and microfluidise at 800 bar×3 passes. Mix the protein-sugar solution and microfluidised Hylon VII dispersion together. Add the oil and homogenise at 250 bar. Cool down to 10° C. Add the freeze dried bacteria into the emulsion using a mixer. Spray dry at 160/65° C. $T_i/T_o$.

| Ingredient | % in powder | % in emulsion |
|---|---|---|
| Freeze dried bacteria | 8% | 2% |
| Na Caseinate | 20% | 5% |
| Oligosaccharide | 20% | 5% |
| Water | | 30% |
| Hylon VII | 20% | 5% |
| Water | | 45% |
| Canola Oil | 32% | 8% |
| Total | 100.0% | 100.0% |

Strategy 3

Example 8

Encapsulated: (In Oil) Protein-Sugar

Freeze dried probiotic bacteria in oil and encapsulated in protein-sugar matrix
Processing Steps Prepare a mixture containing sodium caseinate, oligosaccharide and dried glucose syrup (Cas-oligo-DGS) solution at 60° C. Cool down to 10° C. Disperse freeze dried bacteria in oil. Add the freeze dried bacteria dispersion into the solution using a mixer. Spray dry at 160/65° C. $T_i/T_o$.

| Ingredient | % in powder | % in emulsion |
|---|---|---|
| Freeze dried bacteria | 10% | 3.0% |
| Canola oil | 40% | 12.0% |
| Cas-Oligo-DGS Blend | 50% | 15.0% |
| Water | | 70.0% |
| Total | 100% | 100.0% |

Example 9

Encapsulated: (In Oil) Protein-Sugar MRP

Freeze dried probiotic bacteria in oil and encapsulated in heat reacted protein-sugar matrix
Processing Steps Prepare a mixture containing sodium caseinate, oligosaccharide and dried glucose syrup (Cas-oligo-DGS) solution at 60° C. Heat mixture at 98° C. for 30 min Cool down to 10° C. Disperse freeze dried bacteria in oil. Add the bifido bacteria Bb12 dispersion into the solution using a mixer. Spray dry at 160/65° C. $T_i/T_o$.

| Ingredient | % in powder | % in emulsion |
|---|---|---|
| Formulation 1 | | |
| Freeze dried bacteria | 10% | 3.0% |
| Canola oil | 40% | 12.0% |
| Heat processed Cas-Oligo-DGS | 50% | 15.0% |
| Water | | 70.0% |
| Total | 100% | 100.0% |
| Formulation 2 | | |
| Freeze dried bacteria | 8% | 2.0% |
| Canola oil | 32% | 8.0% |
| Heat processed Cas-Oligo-DGS | 60% | 15.0% |
| Water | | 75.0% |
| Total | 100% | 100.0% |

Example 10

Encapsulated: (In Oil) Protein-RS(Raw)

Freeze dried probiotic bacteria in oil and encapsulated in protein-high amylose starch matrix
Processing Steps Prepare a 15% w/w sodium caseinate solution at 60° C. Prepare a 10% w/w Hylon VII dispersion at 60° C. Mix the sodium caseinate solution and Hylon VII dispersion together. Cool down to 10° C. Disperse freeze dried bacteria in oil. Add the freeze dried bacteria dispersion into the protein-starch mixture using a mixer. Spray dry at 160/65° C. $T_i/T_o$.

| Ingredient | % in powder | % in emulsion |
|---|---|---|
| Freeze dried bacteria | 5% | 0.8% |
| Canola Oil | 20% | 3.1% |
| Na Caseinate | 37.5% | 5.8% |
| Water | | 32.7% |

-continued

| Ingredient | % in powder | % in emulsion |
|---|---|---|
| Hylon VII | 37.5% | 5.8% |
| Water | | 51.8% |
| Total | 100.0% | 100.0% |

Example 11

Encapsulated: (in Oil) Protein-RS(MF)

Freeze dried probiotic bacteria in oil and encapsulated in protein-microfluidised high amylose starch matrix Processing Steps Prepare 15% w/w caseinate solution at 60° C. Prepare 20% w/w Hylon VII dispersion at 60° C., heat 121° C. for 60 min, cool down, and add remaining water to make up to 10% w/w total solids and microfluidise at 800 bar. Mix the sodium caseinate solution and microfluidised Hylon VII together. Cool down to 10° C. Disperse freeze dried bacteria in oil. Add the freeze dried bacteria dispersion into the protein-starch mixture using a mixer. Spray dry at 160/65° C. $T_i/T_o$.

| Ingredient | % in powder | % in emulsion |
|---|---|---|
| Freeze dried bacteria | 5.0% | 0.8% |
| Canola oil | 20.0% | 3.1% |
| Na Caseinate | 37.5% | 5.8% |
| Water | | 32.7% |
| Hylon VII | 37.5% | 5.8% |
| Water | | 51.8% |
| Total | 100.0% | 100.0% |

Example 12

Encapsulated: (In Oil) Protein-Sugar-RS(MF)

Freeze dried probiotic bacteria in oil and encapsulated in protein-sugar-microfluidised high amylose starch matrix Processing Steps Prepare a 15% w/w protein solution at 60° C., then add the sugar. Prepare 20% w/w Hylon VII dispersion at 60° C., heat 121° C. for 60 min, cool down, and add remaining water to make up to 10% w/w total solids and microfluidise at 800 bar×3 passes. Mix the protein-sugar solution and microfluidised Hylon VII dispersion together. Cool down to 10° C. Disperse freeze dried bacteria in oil. Add the freeze dried bacteria dispersion into the protein-starch mixture using a mixer. Spray dry at 160/65° C. $T_i/T_o$.

| Ingredient | % in powder | % in emulsion |
|---|---|---|
| Freeze dried bacteria | 8% | 2% |
| Canola Oil | 32% | 8% |
| Na Caseinate | 20% | 5% |
| Oligosaccharide | 20% | 5% |
| Water | | 30% |
| Hylon VII | 20% | 5% |
| Water | | 45% |
| Total | 100% | 100% |

Assessment of Bacterial Viability

In order to enumerate viable bacteria, the probiotics were released from the microcapsules by dissolving the capsule material in Simulated Intestinal Fluid (SIF) (described later) or deionized water (DI). Duplicate 1.0 g samples of spray-dried encapsulated material were mixed with 10 ml of SIF or DI and the samples were incubated for 1-2 h at 37° C. while continually mixed at 100 rpm. Enumeration of released viable bacteria was conducted using traditional microbiological plating methods. Ten-fold serial dilutions of the released bacteria were performed in 0.1% peptone (pH 6.9-7.0). To facilitate dispersion of the bacteria from oil in the samples Tween 80 (100 μl) was added to the first dilution of all the samples before vortexing. Bifidobacteria were cultured on Reinforced Clostridial Agar (RCA) and the lactobacilli were grown on MRS (de Man, Rogosa and Sharpe) agar. The agar plates were incubated anaerobically for 48 h at 37° C. and CFU/g of encapsulated material was determined. Percent survival was calculated as:

Percent survival=(post-treatment CFU/g÷initial CFU/g)×100%

The advantages of microencapsulation treatments on the survival of probiotic bacteria were examined in four areas:
Survival during spray drying
Survival (and release) during gastrointestinal transit
Survival during non-refrigerated storage
Survival at low pH Advantage of Microencapsulation During Spray Drying Each of the three probiotic bacterial strains mentioned previously was microencapsulated and spray dried using the techniques described in the examples. The percentage of the probiotic bacteria that survived spray drying was determined for each microencapsulation technique. For *Bifidobacterium infantis*, it was possible to spray dry a re-suspended freeze dried sample of bacteria to provide a comparison of the survival of encapsulated and re-suspended freeze-dried bacteria during spray drying.

Figure 1:
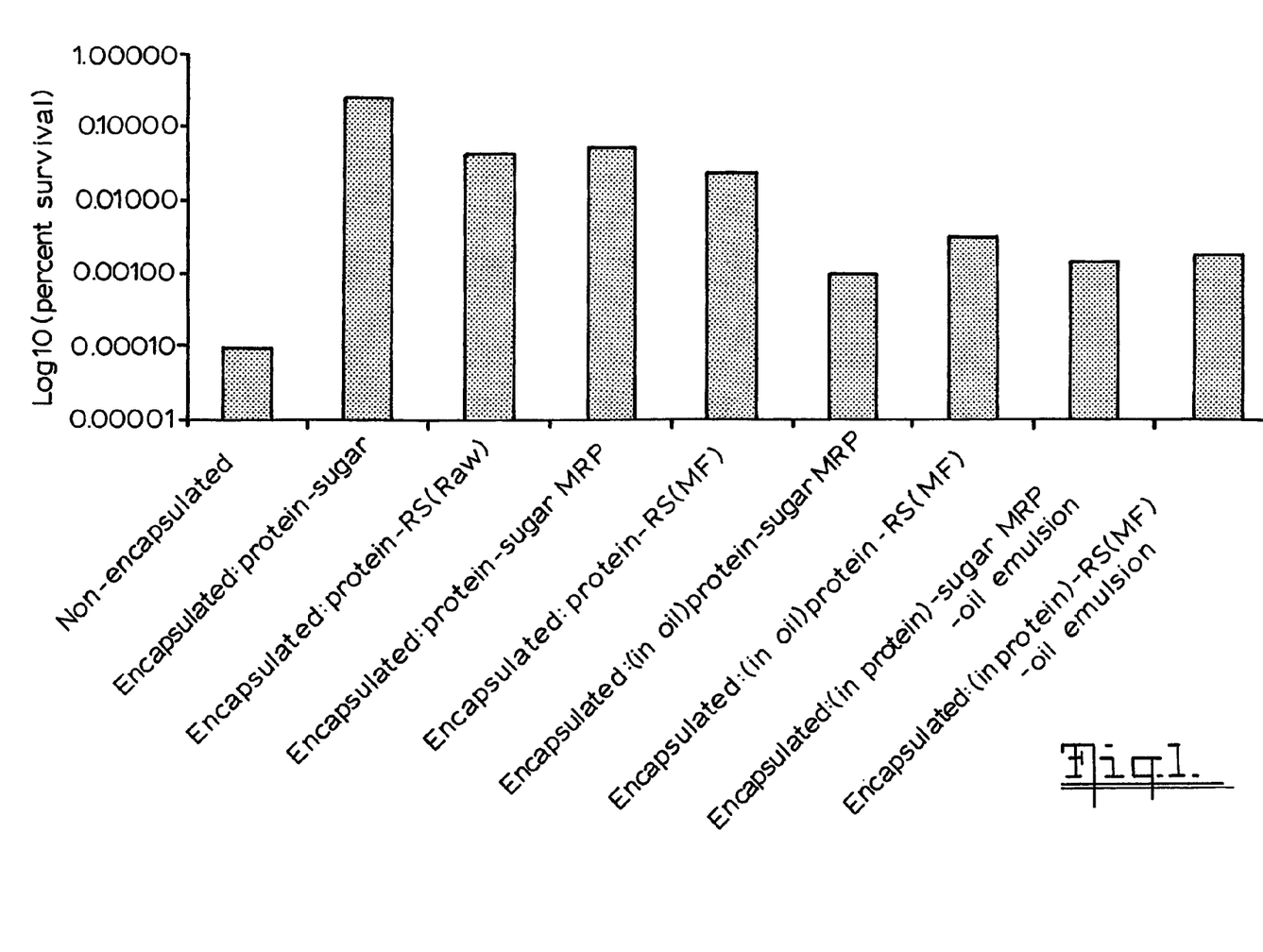
FIG. 1 illustrates graphically the survival of *Bifidobacterium infantis* during spray drying.

FIG. 1 shows that all three microencapsulation strategies protected the probiotic during spray drying compared to non-encapsulated bacteria. ("Non-encapsulated" in FIG. 1 means the freeze dried probiotic sample was dispersed in water and spray dried)

Microencapsulation substantially protected the viability of the probiotic *Bifidobacterium* during spray drying.

Strategy 1 appeared to be the best for *Bifidobacterium infantis* during spray drying. Greater than 3 orders of magnitude (3 $\log_{10}$ units) improvement in the viability of the probiotic was achieved with this sensitive strain.

Figure 2:
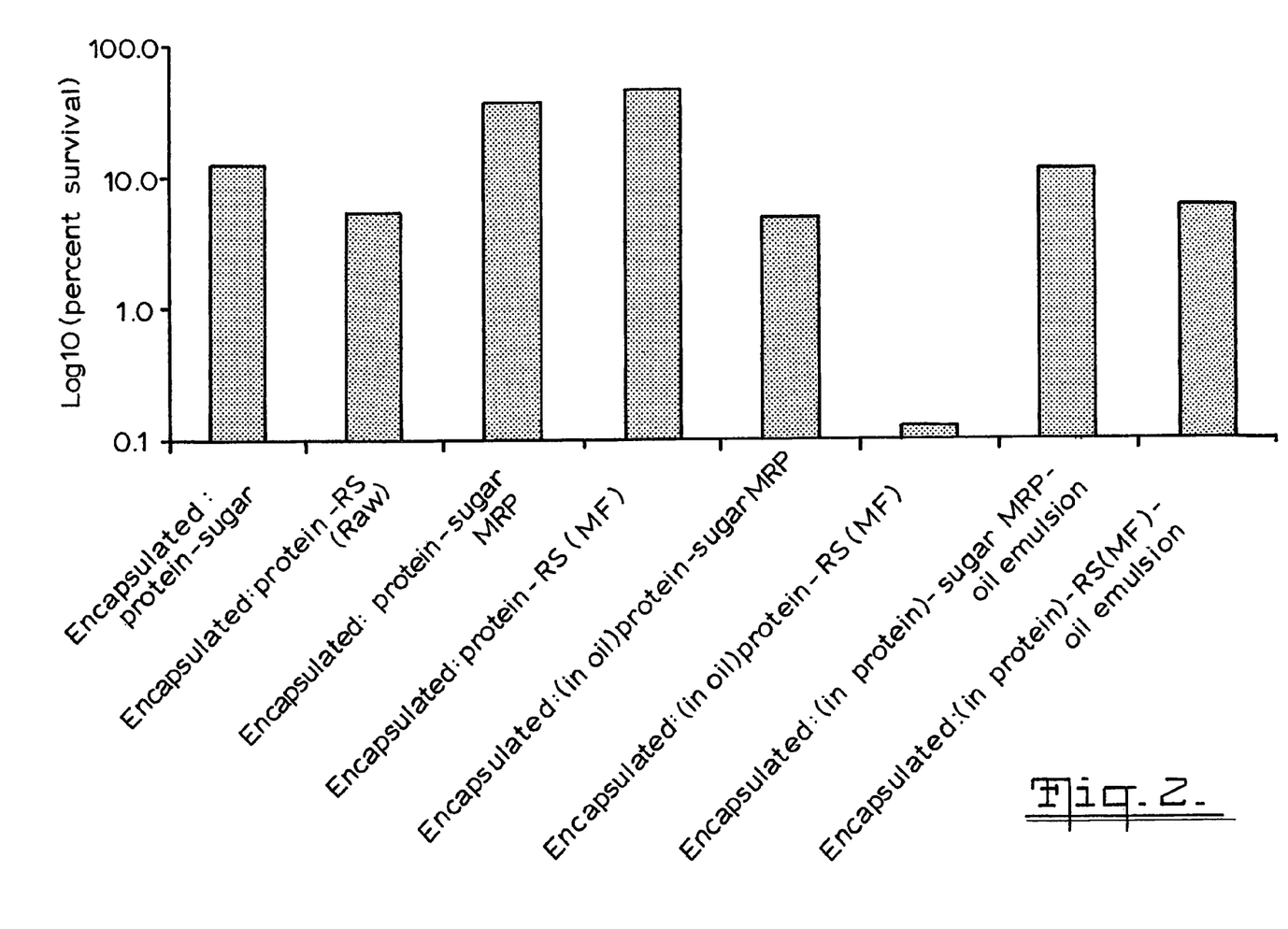
FIG. 2 illustrates graphically the survival of *Bifidobacterium lactis* Bb-12 during spray drying.

FIG. 2 shows that the survival of *Bifidobacterium lactis* Bb-12 is generally much higher than for the sensitive *Bifidobacterium infantis* strain.

A number of microencapsulation treatments enabled the viability of *Bifidobacterium lactis* Bb-12 to be retained within the same order of magnitude (less than 1 $\log_{10}$ drop in viability) during spray drying.

Differences were observed between treatments within Strategy 3 in their ability to protect the viability if *Bifidobacterium lactis* Bb-12.

Since freeze-dried *Bifidobacterium lactis* Bb-12 re-suspended in water could not be spray dried, it was not possible to compare the effects of encapsulation during spray drying for this strain.

Figure 3:
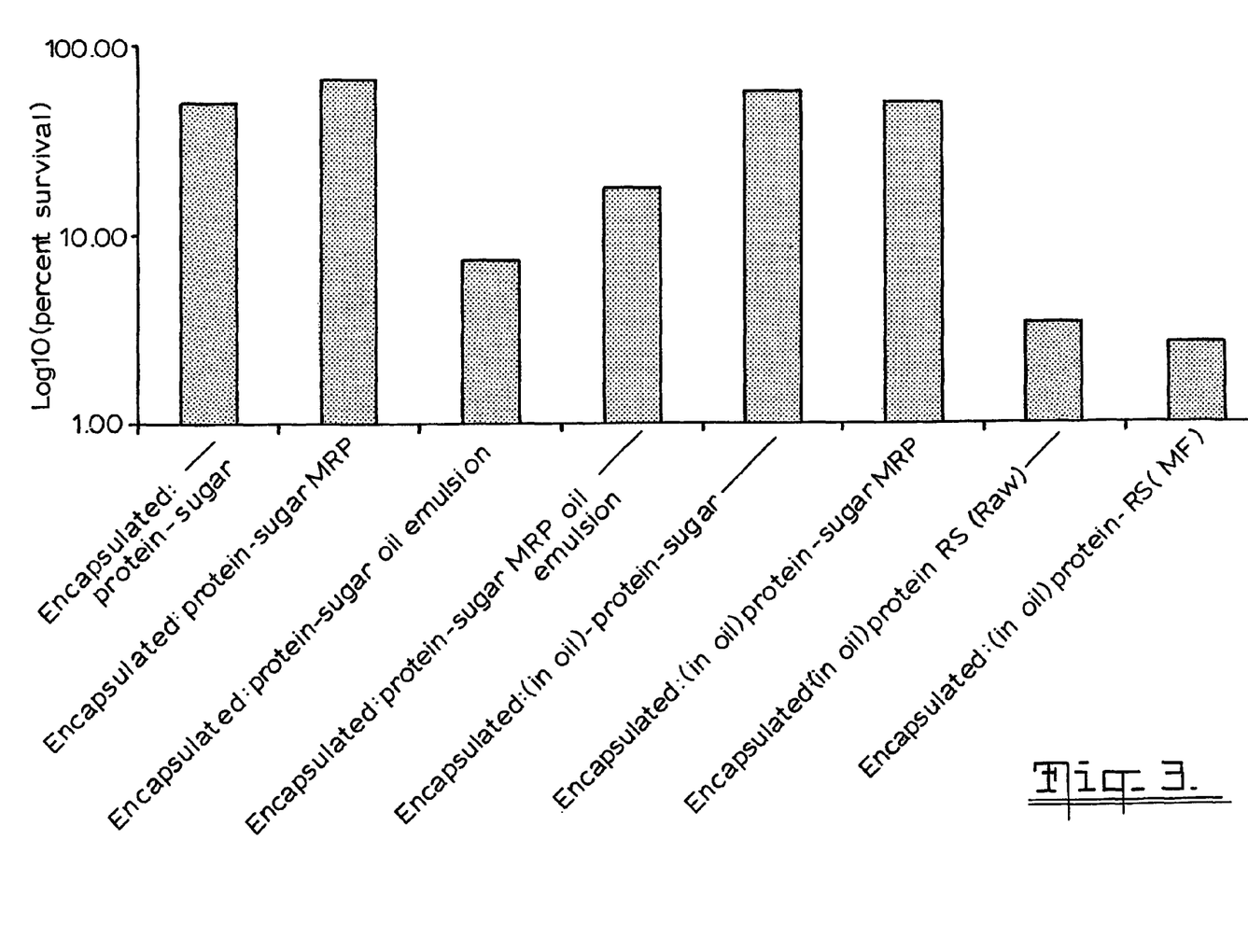
FIG. 3 illustrates graphically the survival of *Lactobacillus acidophilus* La-5 during spray drying.

FIG. 3 shows that the viability of *Lactobacillus acidophilus* La-5 was well maintained during spray drying for a number of encapsulation treatments.

Many microencapsulation treatments allowed greater than 50% viability to be maintained during spray drying with strain-to-strain variation in the most effective treatments.

Overall, FIG. 1 shows that the encapsulation strategies used protect during spray drying, and FIGS. 2 and 3 show that the viability of *Bifidobacterium lactis* Bb-12 and *Lactobacillus acidophilus* La-5 remained largely intact following spray drying.

Advantage of Microencapsulation During Gastrointestinal Transit

To simulate survival during gastrointestinal transit, microencapsulated and non-microencapsulated probiotic bacteria were passed through a two-stage in vitro model simulating conditions in the stomach and small intestine. In stage 1, duplicate 1.0 g samples of each spray-dried encapsulated treatment were mixed in 10 mL of Simulated Gastric Fluid (SGF) and incubated for 2 h at 37° C. with constant agitation at 100 rpm. After 2 hrs, the pH of the samples was adjusted to 6.8 using 1 M sodium hydroxide (added drop wise to prevent possible damage to live cells), then 10 ml of SIF was added to the pH-adjusted sample which was incubated for a further 3 h at 37° C. with constant stirring at 100 rpm. Viable counts of the bacteria were then measured.

The SGF and SIF were prepared as follows (Reference: US Pharmacopea (2000) & National Formulatory (USP 24NF19, Rockville Md.):

Simulated Gastric Fluid (SGF)(pH 1.2)

Sodium chloride (1.0 g), 1.6 g of pepsin, and 3.5 ml of concentrated HCL (36%) were dissolved in deionized water to a final volume of 500 ml. The final pH of the solution was 1.2.

Simulated Intestinal Fluid (SIF)(pH 6.8)

Potassium hydrogen phosphate was prepared by dissolving 3.4 g in 450 ml of deionised water. $T_o$ this, 38.5 ml of 0.2 M sodium hydroxide and 6.25 g of pancreatin (8×USP grade) was added. The solution was mixed at 4° C. overnight and the pH was adjusted to 6.8 with 1 M sodium hydroxide or with 0.2 M hydrochloric acid. The volume was made up to 500 ml with deionized water.

Figure 4:
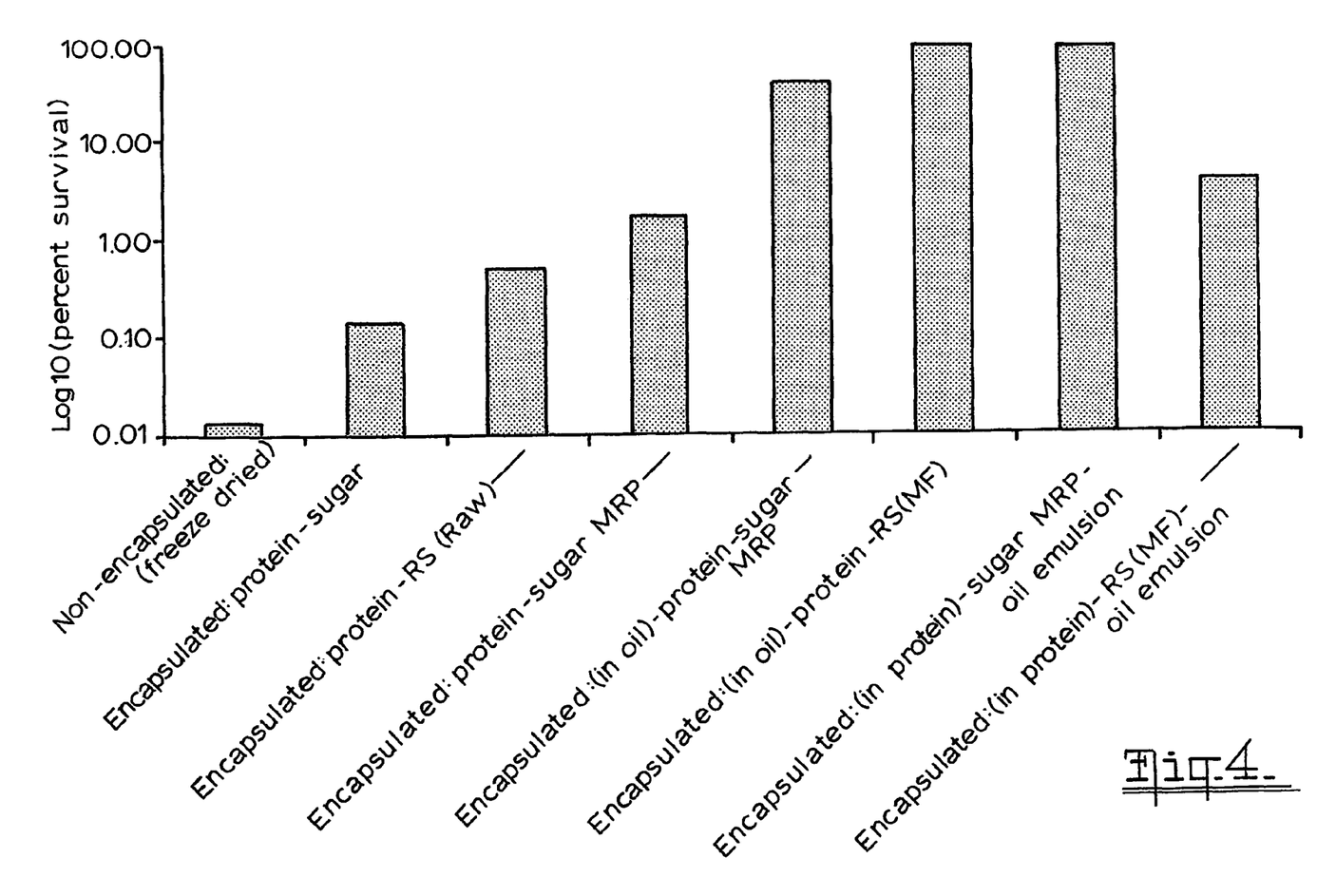
FIG. 4 illustrates graphically the survival of *Bifidobacterium infantis* during simulated gastrointestinal transit.

FIG. 4 shows that all three microencapsulation strategies improved the viability of the strain. ("Non-encapsulated (freeze dried)" means freeze dried probiotic sample in FIG. 4 and all subsequent Figures)

Microencapsulation substantially protected the viability of the probiotic *Bifidobacterium infantis* compared to the non-encapsulated freeze dried bacteria.

Strategies 2 and 3 were the most protective.

Almost 100% survival of this sensitive probiotic strain was achieved with encapsulation compared to non-encapsulated bacteria for which viability dropped by almost 4 orders of magnitude (4 $\log_{10}$ units) under the same conditions.

Advantage of Microencapsulation During Non-refrigerated Storage

The survival of encapsulated and non-encapsulated probiotic bacteria was assessed during storage over a 5-week period at 25° C. and 50% relative humidity. The survival of the bacteria was assessed after 2 weeks and 5 weeks. Viable counts were obtained as described previously.

Figure 5:
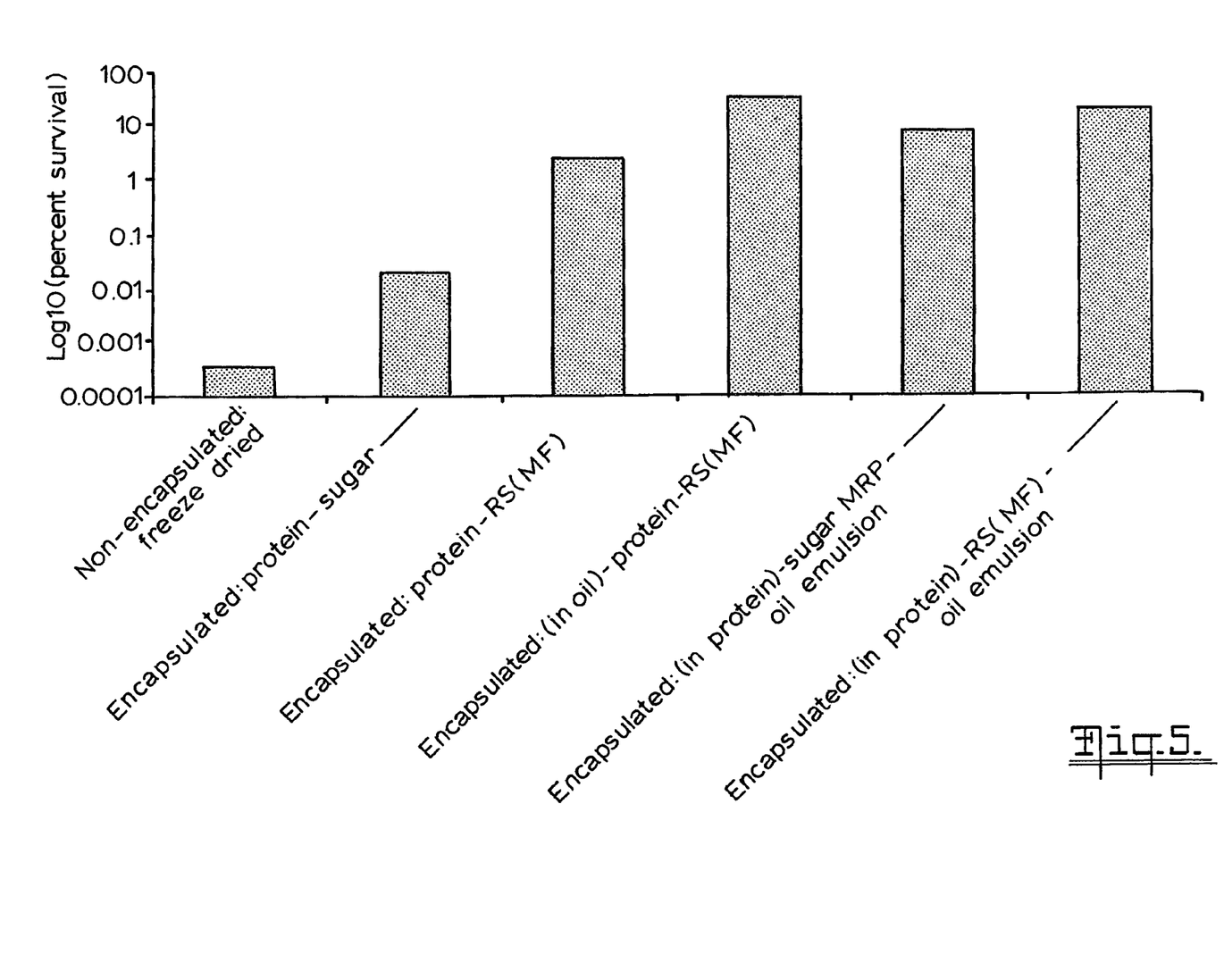
FIG. 5 illustrates graphically the survival of *Bifidobacterium infantis* following storage for 2 weeks at 25° C. and 50% relative humidity.

FIG. 5 shows that all three microencapsulation strategies protected the viability of the strain to some extent after 2 weeks storage at 25° C.-50% RH. Microencapsulation substantially protected the viability of the probiotic FIG. 4 shows that all three microencapsulation strategies improved the viability of the strain. ("Non-encapsulated (freeze dried)" means freeze dried probiotic sample in FIG. 4 and all subsequent Figures)

Microencapsulation substantially protected the viability of the probiotic *Bifidobacterium infantis* compared to the non-encapsulated freeze dried bacteria. compared to the non-encapsulated bacteria during non-refrigerated storage. Strategies 2 and 3 were the most protective.

The viability of this probiotic strain, from a species that is sensitive to environmental conditions such as oxygen, was maintained within the same order of magnitude (less than 1 $\log_{10}$ unit drop) over a 2-week period in non-refrigerated conditions using some treatments.

In contrast, the viability of non-encapsulated freeze dried bacteria was reduced by more than 5 orders of magnitude.

Figure 6:
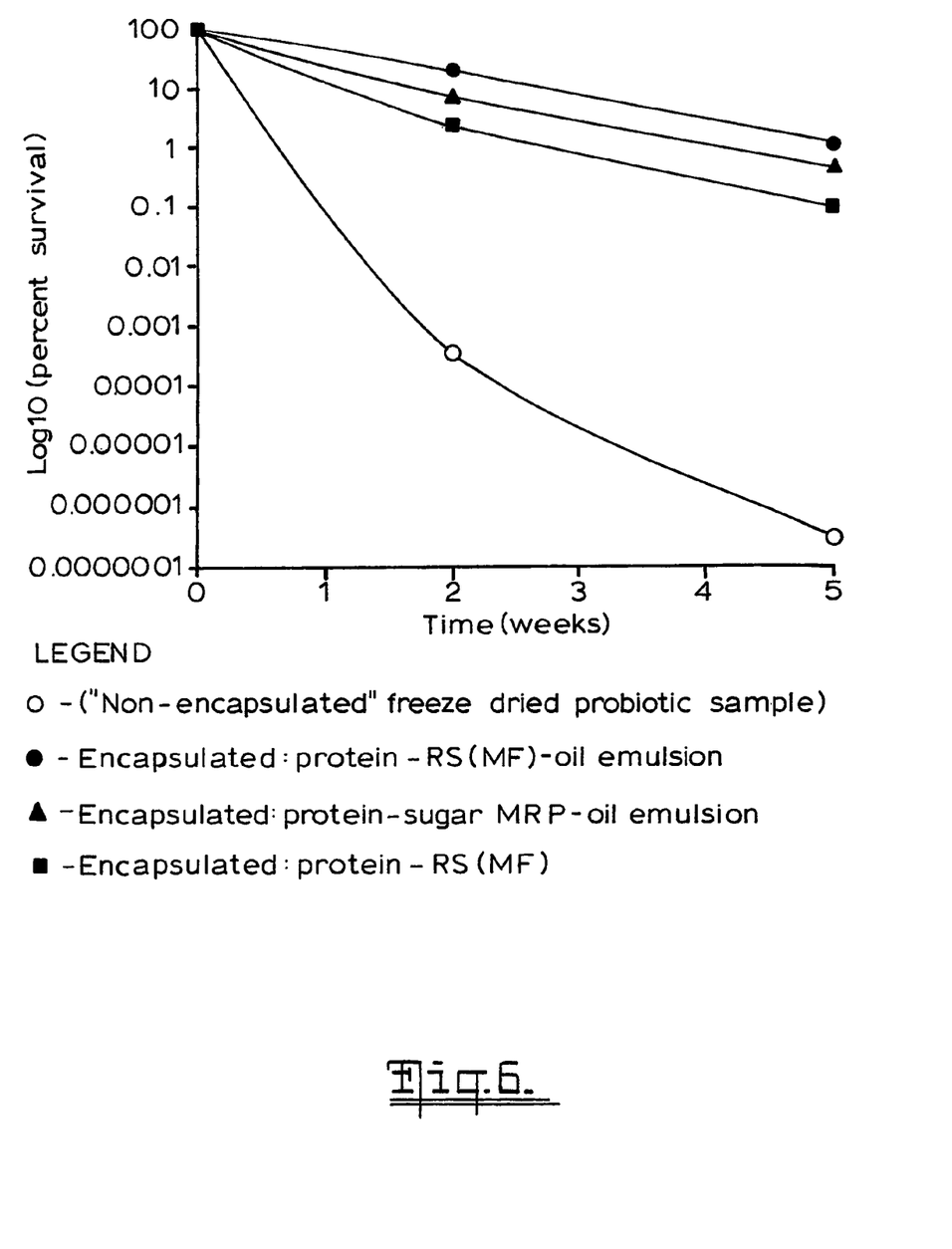
FIG. 6 illustrates graphically the survival of *Bifidobacterium infantis* during storage for 5 weeks at 25° C. and 50% relative humidity.

FIG. 6 shows that microencapsulation substantially protected the viability of the probiotic *Bifidobacterium infantis* compared to the non-encapsulated bacteria during non-refrigerated storage. After 5 weeks of storage, the treatments encompassing Strategy 2 and encapsulation in protein-RS (MF) (Strategy 1) were the most successful at maintaining the viability of *Bifidobacterium infantis*.

After storage at 25° C. and 50% relative humidity for 5 weeks, microencapsulation of the bacteria using Strategy 2 enabled the loss in viable counts to be maintained at less than 2 $\log_{10}$ units, compared to a greater than 8 $\log_{10}$ unit drop in viable counts observed for non-encapsulated bacteria.

Figure 7:
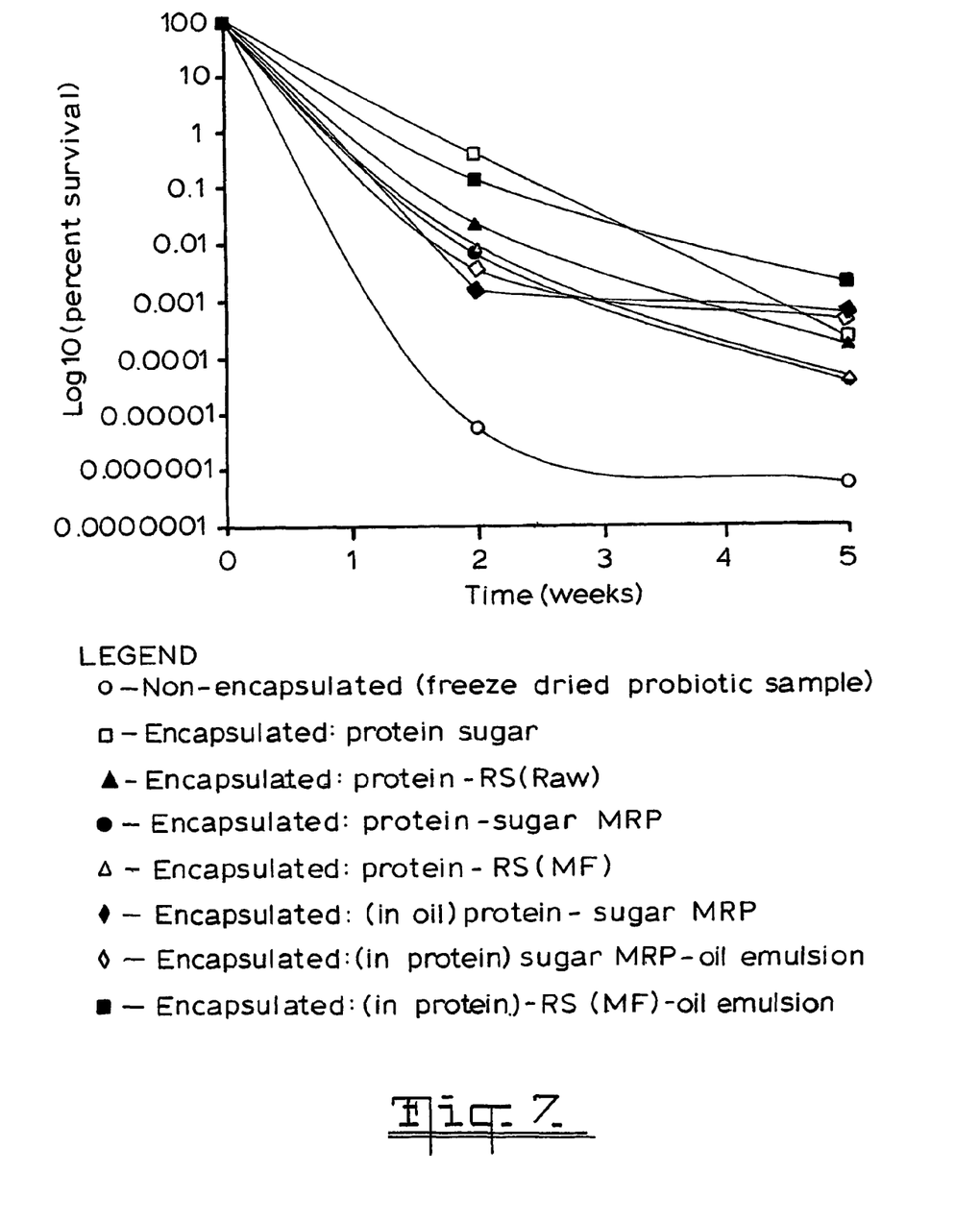
FIG. 7 illustrates graphically the survival of *Bifidobacterium lactis* Bb-12 during storage for 5 weeks at 25° C. and 50% relative humidity.

FIG. 7 shows that all three microencapsulation strategies protected the viability of the strain during storage for 5 weeks at 25° C. and 50% relative humidity to a greater degree than non-encapsulated bacteria.

Microencapsulation substantially protected the viability of the probiotic *Bifidobacterium lactis* Bb-12 compared to the non-encapsulated freeze dried bacteria during non-refrigerated storage. The viability of the non-encapsulated bacteria at 2 weeks storage was below the detection limit of 1000 CFU/g. The percent survival depicted for non-encapsulated freeze dried bacteria at this point therefore represents the maximum possible percent survival and may be an overestimate.

The benefit in terms of percent survival after 5 weeks was between 2 and 4 $\log_{10}$ units.

Advantage of Microencapsulation in a Low pH Environment

The ability of the microcapsules to protect the bacteria against moderately low pH was assessed using incubation at pH 4.0 as an example. Encapsulated spray dried and non-encapsulated freeze dried probiotic bacteria (0.12 g freeze dried powder equivalent) were mixed in 10 mL of 0.2 M acetate buffer at pH 4.0 and incubated for 2 hrs at 37° C. with constant stirring at 100 rpm. Following the 2 h incubation, the pH of the samples was adjusted to 6.8 using 1 M sodium hydroxide and they were incubated for a further 1 h at 37° C. (room temperature) to effect release of the bacteria from the capsules. The viable counts of bacteria in the samples were determined as described previously.

Figure 8:
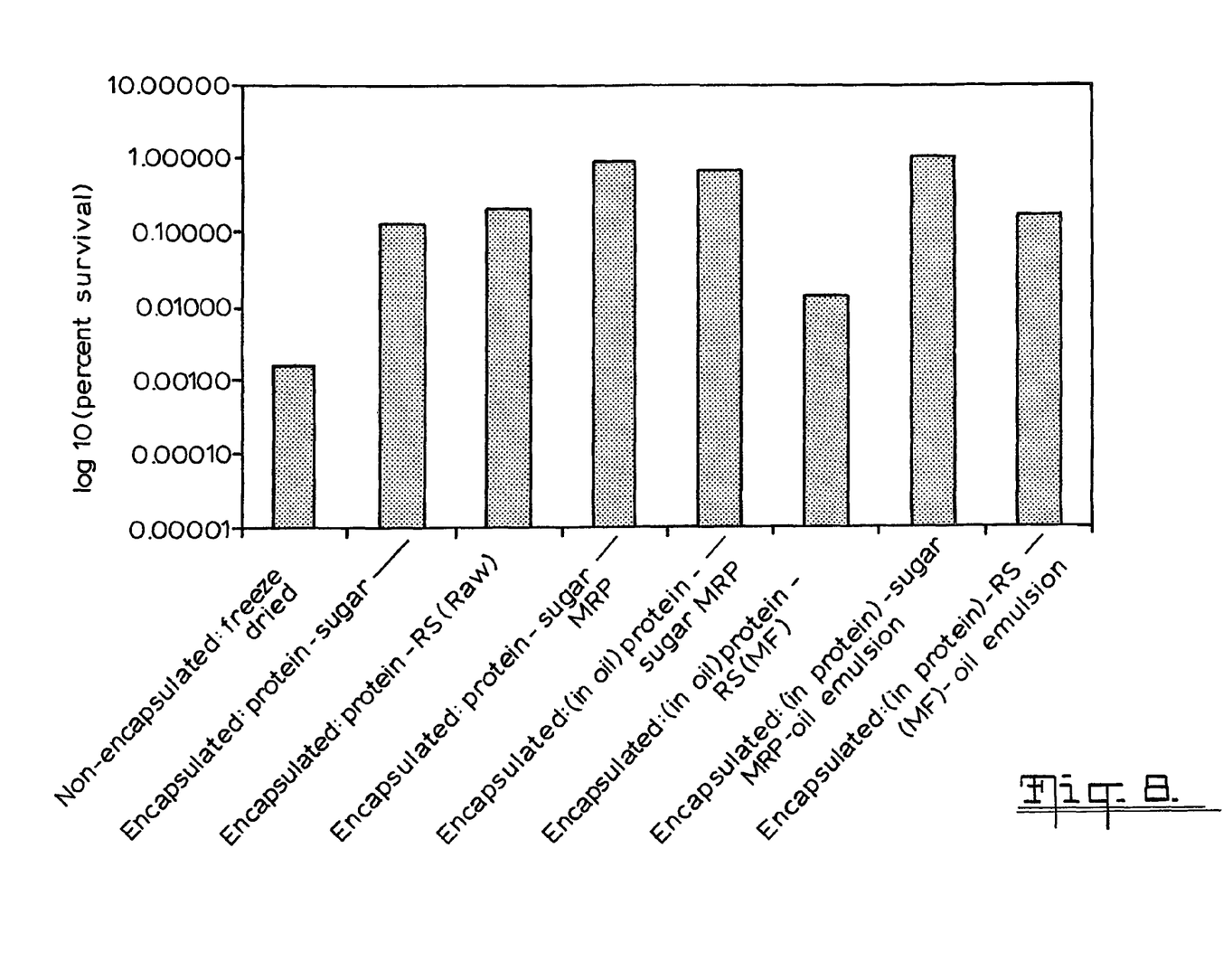
FIG. 8 illustrates graphically the survival of *Bifidobacterium infantis* following incubation at pH 4.0 for 2 hours.

FIG. 8 shows that all three microencapsulation strategies protected the viability of the strain to some extent, providing on average a 2-3 log improvement in viability following incubation at pH 4.0. ("Non-encapsulated: freeze dried" is the freeze dried probiotic sample)

Microencapsulation substantially protected the viability of the probiotic *Bifidobacterium infantis* compared to the non-encapsulated freeze dried bacteria.

Those skilled in the art will realize that this invention may be realized in embodiments differing from those described without departing from the basic teachings of the invention.

The invention claimed is:

1. An encapsulated probiotic in which one or more probiotic microorganisms are encapsulated in a protective encapsulant matrix to prolong the storage life of the probiotic, wherein the encapsulant matrix is formed by the combination of a film-firming protein and a carbohydrate in which the encapsulation in the matrix is achieved by a) mixing a water-dispersible probiotic microorganism in an aqueous suspension of the film-forming protein and the carbohydrate, b) mixing an oil-dispersible probiotic microorganism in an oil-in-water emulsion of the film-forming protein, the carbohydrate, and a fat, or c) mixing the probiotic microorganism in an oil that subsequently is dispersed in an aqueous dispersion of the film-forming protein and the carbohydrate.

2. The encapsulated probiotic as claimed in claim 1, wherein the carbohydrate contains a reducing sugar group.

3. The encapsulated probiotic microorganism as claimed in claim 1 or 2, wherein one or more prebiotic materials are mixed with the probiotic microorganisms.

4. The encapsulated probiotic microorganism as claimed in claim 1 or 2, wherein the carbohydrate in the film-forming composition is a prebiotic carbohydrate.

5. The encapsulated probiotic microorganism as claimed in claim 1, wherein the protein is casein or whey protein.

6. The encapsulated probiotic microorganism as claimed in claim 1 or 2, wherein the carbohydrate is a resistant starch or a high-amylose starch.

7. The encapsulated probiotic bacteria as claimed in claim 2, wherein the protein and carbohydrate are heat processed.

8. The encapsulated probiotic microorganism as claimed in claim 2, wherein the protein and carbohydrate are heat processed in the presence of an oil or fat prior to addition of the probiotic bacteria.

9. The encapsulated probiotic microorganism in claim 3, wherein the starch is processed by heating and/or microfluidisation.

10. The encapsulated probiotic microorganism as claimed in claim 1 which is spray dried or freeze dried to form a powder.

11. The encapsulated probiotic microorganism as claimed in claim 1 in which the probiotic microorganism is selected from the group consisting of bifidobacteria, lactobacilli, *saccharomyces*, lactococci, streptococci, and propionibacteria.

12. The probiotic powder of claim 10, wherein the probiotic microorganism is selected from the group consisting of bifidobacteria, lactobacilli, *saccharomyces*, lactococci streptococci and propionibacteria, wherein the film-forming protein is casein or whey protein, and wherein the carbohydrate is an oligosacharride.

13. The probiotic powder of claim 12 in which the encapsulant matrix has been heated to form Maillard reaction products between the oligosaccharide and the casein or whey protein.

14. The probiotic powder of claim 12 in which the probiotic microorganism is a liquid probiotic concentrate.

15. The probiotic powder of claim 12 in which the probiotic microorganism is freeze dried.

* * * * *